United States Patent [19]
Conlan et al.

[11] Patent Number: 5,769,794
[45] Date of Patent: Jun. 23, 1998

[54] TISSUE RETRIEVAL BAG AND METHOD FOR REMOVING CANCEROUS TISSUE

[75] Inventors: A. Alan Conlan, Worcester; Yuri E. Kazakevich, Andover; Steven W. Ek, Bolton; Babs R. Soller, Northboro, all of Mass.

[73] Assignees: Smith & Nephew Endoscopy, Inc, Andover; University of Massachusetts, Worcester, both of Mass.

[21] Appl. No.: 707,698

[22] Filed: Sep. 4, 1996

[51] Int. Cl.$^6$ .................................................. A61B 10/00
[52] U.S. Cl. .............................................. 600/562; 600/37
[58] Field of Search ........................ 128/846, 849–856, 128/888, DIG. 24, 749; 600/37; 604/327, 328, 356; 606/114, 127, 128

[56] References Cited

U.S. PATENT DOCUMENTS

| | | | |
|---|---|---|---|
| 3,575,225 | 4/1971 | Muheim | 128/DIG. 24 |
| 3,920,179 | 11/1975 | Hall | 128/DIG. 24 |
| 4,867,177 | 9/1989 | Urheim | 128/856 |
| 5,037,379 | 8/1991 | Clayman et al. | 600/37 |
| 5,074,867 | 12/1991 | Wilk | 606/128 |
| 5,147,371 | 9/1992 | Washington et al. | 606/127 |
| 5,190,555 | 3/1993 | Wetter et al. | 606/114 |
| 5,192,284 | 3/1993 | Pleatman | 606/114 |
| 5,215,521 | 6/1993 | Cochran et al. | 604/22 |
| 5,290,305 | 3/1994 | Inoue | 606/191 |
| 5,312,416 | 5/1994 | Spaeth et al. | 606/114 |
| 5,330,483 | 7/1994 | Heaven et al. | 606/114 |
| 5,337,754 | 8/1994 | Heaven | 128/DIG. 24 |
| 5,353,784 | 10/1994 | Nady-Mohamed | 128/20 |
| 5,368,545 | 11/1994 | Schaller et al. | 600/37 |
| 5,370,647 | 12/1994 | Graber et al. | 606/127 |
| 5,459,879 | 10/1995 | Fuchs | 2/161.7 |
| 5,465,731 | 11/1995 | Bell et al. | 128/749 |
| 5,486,182 | 1/1996 | Nakao et al. | 606/114 |
| 5,499,988 | 3/1996 | Espiner et al. | 606/114 |
| 5,524,633 | 6/1996 | Heaven | 128/DIG. 24 |
| 5,524,644 | 6/1996 | Crook | 128/888 |

OTHER PUBLICATIONS

Clayman, R. et al., "Laparoscopic Nephrectomy: Initial Case Report," *The Journal of Urology*, vol. 146, 278–282 (1991).
Product Descriptions: Straight Disposable Blades, Curved Disposable Blades and Straight Disposable Burrs, Smith & Nephew Endoscopy Inc., (3 pages).
Urban, D. et al., "Organ Entrapment and Renal Morcellation: Permeability Studies," *The Journal of Urology*, vol. 150, 1792–1794 (1993).

*Primary Examiner*—Michael A. Brown
*Attorney, Agent, or Firm*—Lahive & Cockfield, LLP

[57] ABSTRACT

A tissue retrieval bag has a wide mouth and folds for insertion through an incision to a body cavity to form a flat tray and receive excised tissue. The tissue is dropped onto the floor of the bag and the mouth of the bag is then drawn back through the incision, where it drapes the opening to provide a protected tunnel to the resected tissue still lying within the cavity. The bag is preferably transparent, and the enclosed tissue may be viewed endoscopically while a morcellizer is inserted through the tunnel and operated to aspirate the tissue, so that the bag is then readily withdrawn through the incision. Alternatively, an endoscope may be inserted through the tunnel directly into the bag to monitor and control morcellation. In a preferred embodiment the tissue is resected lung tissue and, a morcellizer blade is used to selectively morcellate only the parenchyma, leaving lymphatic tissue and the bronchial tree in the bag for histologic analysis. The bag may have pleated walls which provide dimensional stability in a shape that avoids cutter damage and cleanly catches and contains the resected tissue, thus reducing the risk of seeding tumor cells.

20 Claims, 7 Drawing Sheets

TISSUE RETRIEVAL BAG AND METHOD FOR REMOVING CANCEROUS TISSUE

BACKGROUND

The present invention relates to the removal of tissue from a surgical site, and more particularly to the removal of excised tissue from an endoscopically accessed surgical arena. In particular, the invention relates to a novel tissue retrieval bag, and to methods of use of the bag.

Minimally invasive or video assisted surgical procedures are being developed now at a great pace for replacing a number of conventional surgical procedures. Such minimally invasive surgery generally involves performing operations within a body cavity without cutting down to or opening up an exposed operating arena. The surgery uses many of the same implements originally developed for working in joint spaces without destroying the surrounding vascular and connective tissue. Surgeons are now applying this approach to major operations in the thoracic and peritoneal cavities. The new techniques reduce the amount of cutting and trauma associated with an operation, and in many cases reduce secondary complications and consequently the medical costs associated with longer hospital stays.

The performance of such minimally invasive or endoscopic surgery generally involves making a small incision, inserting an endoscope to the operative arena and providing several additional incisions or openings through which surgical implements, e.g. tools for cutting, manipulation and suturing are introduced. The closed body cavity is illuminated, and is viewed through a video camera while the surgeon performs surgery. The principal limitation of this approach, which has required the development of many new surgical implements and techniques, is that the incisions through which the surgeon accesses the tissue site are small, and dependable techniques have to be developed for the various acts of cutting, suturing and removing the excised tissue.

The problems associated with removing excised tissue are grave when dealing with infected or tumorous material. In this case the possibility of seeding the disease to other sites is great, and care must be exercised to avoid contact with surrounding tissue. This is particularly difficult when removing large amounts of tissue or large sized organs through a relatively small incision which may, for example, be only four centimeters or less in length.

To address this problem a number of tissue retrieval sacks have been developed which are fitted through an incision comparable in size to the incision provided for the endoscope, and are placed within the surgical cavity, where the surgeon may manipulate pieces of tissue into the sack to isolate it from contact with healthy tissue. Such tissue retrieval bags are generally relatively long and narrow, like sausage casings, and may be provided with a purse string to close the end and allow the sack with its contents to be pulled back through the access incision. However, when large masses of tissue are excised the contents of the bag may be too great for removal in this fashion. Some surgeons have reported inserting a morcellizer through the neck of the bag to chop up and aspirate tissue before withdrawing the bag. When this is done, care must be taken to not puncture the bag, as the morcellizer splatters and introduces a great deal of dispersion of tissue so that any leakage may seed tumor cells. Thus, concomitant with the convenience of reducing the mass of tissue to be pulled back out through the access incision, the morcellizer greatly increases the likelihood of contamination should any leakage from the bag occur. Furthermore, when using a morcellizer questions also arise as to the integrity of tissue so removed. If the morcellizer cuts relatively clean slices, the aspirated tissue may be suitable for pathology examination; on the other hand if the morcellizer is a relatively high speed blunt homogenizing instrument, then substantially all histologic information from the removed tissue is lost. In either case, it is preferable to morcellate selectively to leave certain pathology samples intact for later analysis. With endoscopic viewing and morcellation, it is difficult to identify tumor margins and ensure that the specimens required by the pathologist retain their integrity.

Thus, it would be desirable to remove tissue without contamination in a tissue retrieval bag, yet exercise a degree of selectivity between healthy and tumorous tissue or between different tissues visualized in the operating arena.

SUMMARY OF THE INVENTION

One or more of the above desirable ends are achieved in accordance with the present invention by providing a tissue retrieval bag for endoscopic surgery wherein the bag has a large self opening mouth or collar and is adapted to be folded and inserted through an incision to lie flat in a body cavity. A method of using the bag involves folding and inserting the bag through the incision to a body cavity, and then while viewing the arena endoscopically placing the tissue on the flat bottom of the bag and raising the sides of the bag back through the access incision. The bag is relatively wide along its whole length so that once the mouth of the bag has been drawn back through the incision the upper portion of the bag drapes the surgical site and provides a protective tunnel from the outside into an enclosed chamber formed by the lower portion of the bag in the operating arena. A morcellizer is then introduced through the mouth of the bag and is operated, under endoscopic viewing, to morcellate the contained tissue. Preferably the bag is substantially transparent and the entire procedure may be viewed through an endoscope located in the surgical cavity. Alternatively, an endoscope may be inserted through the mouth of the bag to view the morcellation.

In a preferred embodiment, the bag is adapted for thoracoscopic surgery, and is of a size to receive a large tissue mass, such as a lobe of the lung or a part thereof. The morcellizer has a tip with a hollow rounded bulbous surface and a blade rotating at high speed just below a window in the surface. The tip geometry defines a selective cutter such that when pressed against soft tissue the blade cuts the tissue and aspirates it out through the handle, while when pressed against harder tissue no cutting occurs. Thus for example when faced with a mass of excised tissue such as normal lung abutting against a physically distinct tissue, e.g., the relatively harder bronchial tree, the morcellizer automatically digests the parenchyma while leaving the margins of lung contiguous to more rigid tissue behind. Thus, tissue selectivity of the morcellizer automatically leaves behind precisely the lymph nodes and tissue required by the pathologist for analyses of cell type, tumor boundaries and detection of processes spreading across tissue types.

In one embodiment, the bag has a substantially cylindrical shape with a flat closed bottom, a cylindrical side wall and an open top. The cylindrical side in another embodiment is formed with one or more horizontal circumferential pleats, or folds, allowing the side to collapse vertically into a neatly compressed ring and lie in a substantially stiff flat disposition at the bottom of the body cavity. The upper part of the bag has a ring embedded within its perimeter forming a circular rim at the mouth of the bag that automatically springs open wide and lies flat. The diameter of the mouth is large, preferably equal to or larger than the diameter of the bottom portion of the bag. Thus, in contrast to conventional narrow neck retrieval bags, the present bag collapses to provide a flat surface onto which tissue is easily and cleanly moved, without contaminating external surfaces of the sides. Preferably all or a portion of the side walls are formed of transparent material, allowing the bag contents to be viewed after the mouth has been drawn back up through the incision and morcellation proceeds.

BRIEF DESCRIPTION OF THE DRAWINGS

These and other features of the invention will be understood from a description of representative embodiments, together with illustrative drawings thereof, wherein.

DETAILED DESCRIPTION

Figure 1:
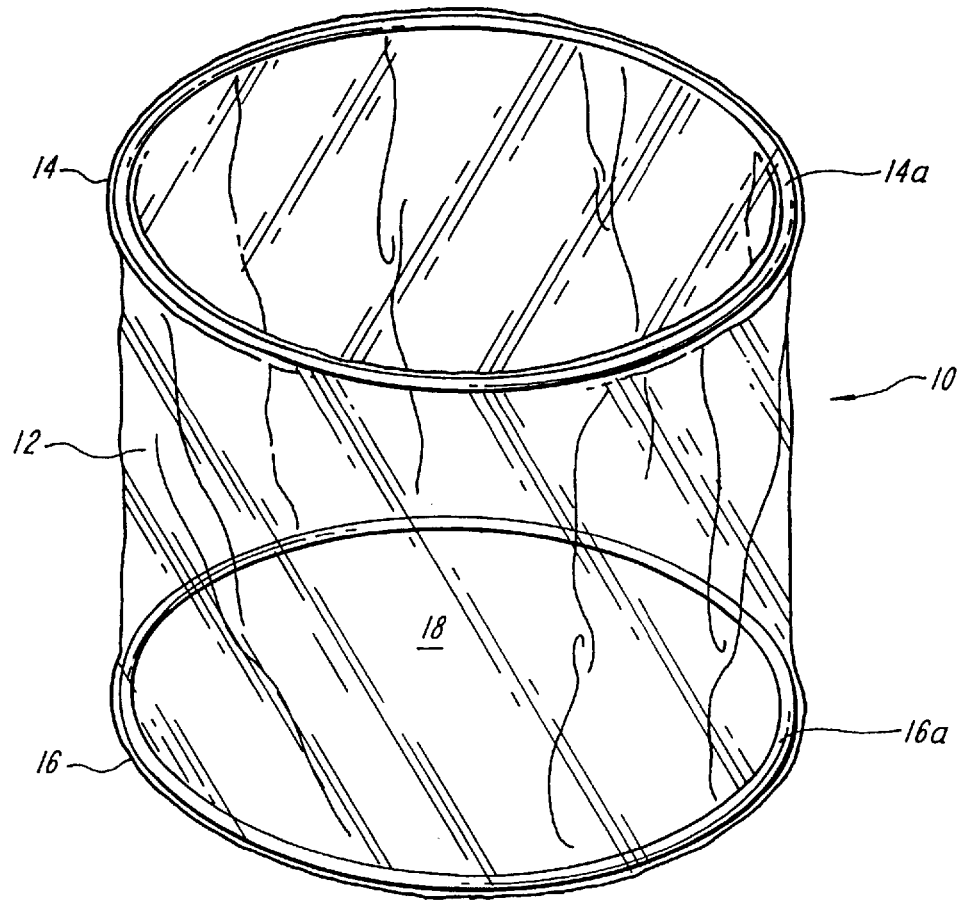
FIG. 1 shows a first embodiment of a tissue retrieval bag of the present invention.

The present invention provides a bag for the retrieval of tissue from endoscopic surgery. FIG. 1 illustrates one prototype embodiment adopted for retrieval of excised or resected tissue in thoracoscopic surgery. The bag 10 is characterized by an overall cylindrical shape having a peripheral wall 12 of a generally cylindrical form, a top rim or edge 14 and a bottom peripheral edge 16. The bag is transparent and has a floor 18 visible through the cylindrical wall 12. At the top and bottom, respective stiffening members 14a and 16a are provided to maintain a circular cross-sectional profile. Each of these may for example be a spring or stiff O-ring such as is commonly used to provide a spring-like stiff but flexible rim. The respective stiffening members 14a, 16a are shown as spiral wound stainless steel coils. Preferably however the members are simple o-rings, formed of a material such as butyl rubber, buna-L, polyethylene or a silicone rubber, although other forms of spring such as articulated or flexible plastic rods or leaf springs may be used. As shown, each of the stiffening/spring members 14a, 16a opens naturally to a circular contour, and thus serves as a stent to spread the floor, and to open the mouth of the bag.

Figure 2:
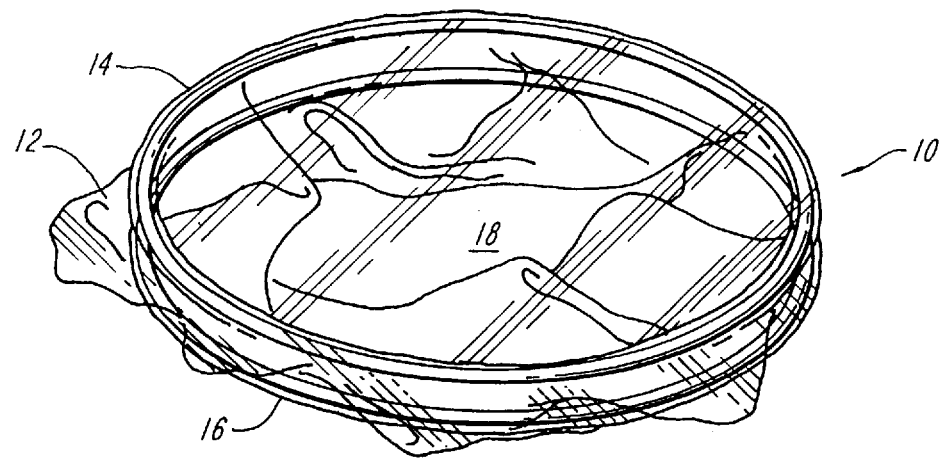
FIG. 2 shows the bag of FIG. 1 in a collapsed state.

FIG. 2 shows the bag 10 of FIG. 1 collapsed. In this configuration, the top rim, 14 has fallen down to approximately the level of the bottom rim 16, while the side wall 12, being relatively flaccid, has simply bundled up or folded around the edge. When so collapsed, the floor 18 lies at substantially the same level as the top and bottom rims and the bunched-in walls 12 lie away from the center of the floor. So collapsed, the shape of the bag is rather like a tray or a cake pan. Thus when inserted into a body opening, the bag may receive tissue by simply sliding the tissue over or lifting it slightly to place it in the center of the flat disc footprint of the collapsed bag.

Figure 3:
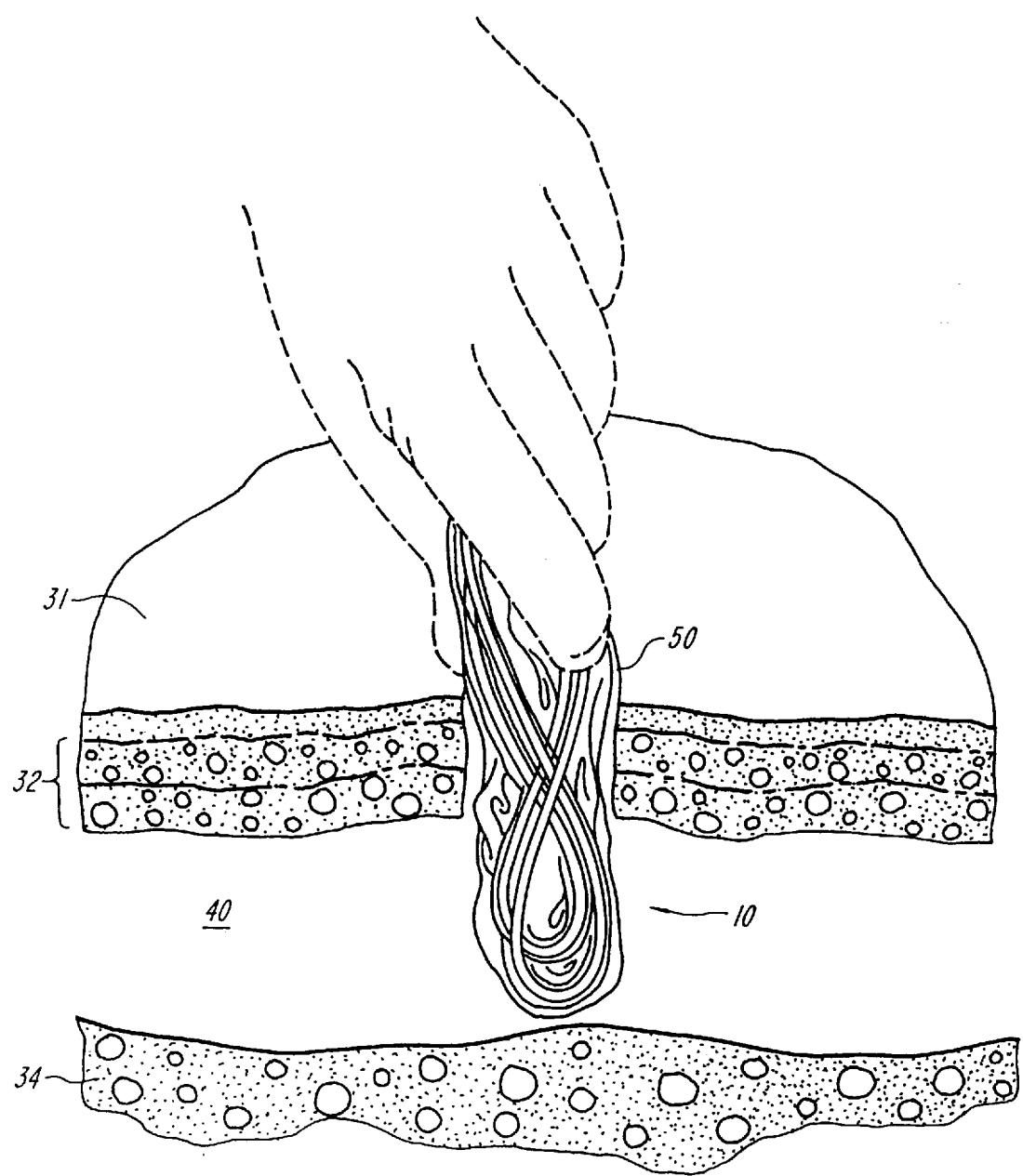
FIG. 3 illustrates an insertion of the bag through a surgical opening to an operative site.

FIG. 3 illustrates insertion of the bag into an endosurgical opening. As shown in FIG. 3, an operative site 40 is situated below the skin 31 and surface tissue layers 32 of a patient, and above other internal tissue 34 such as bone, muscle or surrounding organs. The cavity 40 is an endoscopic surgical cavity, accessed by a slotted incision 50 through the skin. As shown, bag 10 is inserted through the slot incision 50 by folding the bag to reduce its size, and sliding the narrow folded assembly into the cavity 40. The illustration shows the bag twisted, although in practice a simple fold is preferred.

Figure 4:
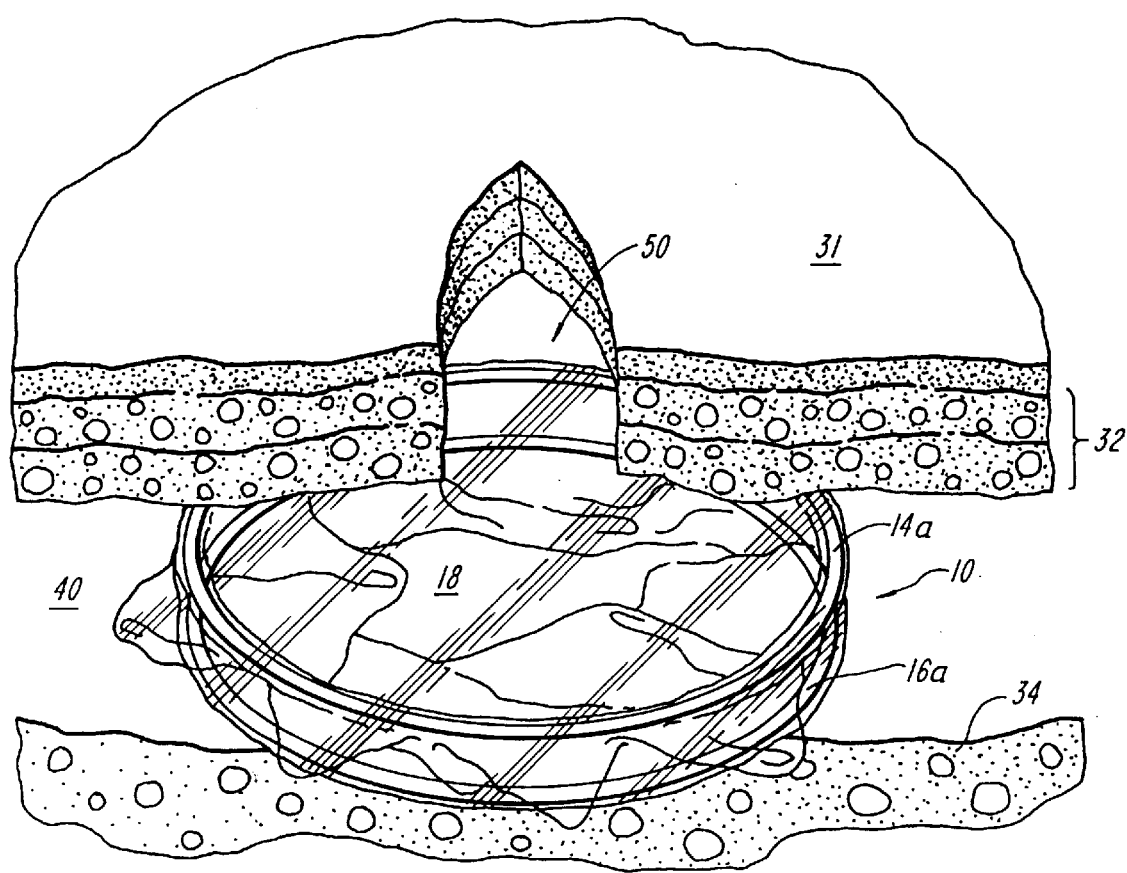
FIG. 4 illustrates the inserted bag in body cavity.

FIG. 4 shows the incision 50 and surgical site 40 of FIG. 3 with the bag 10 fully inserted therein. As shown, the bag has self-opened to form a flat round tray with its floor 18 substantially exposed and the rims 14a, 16a maintaining the bag in this fully extended but flat and open shape.

Figure 8:
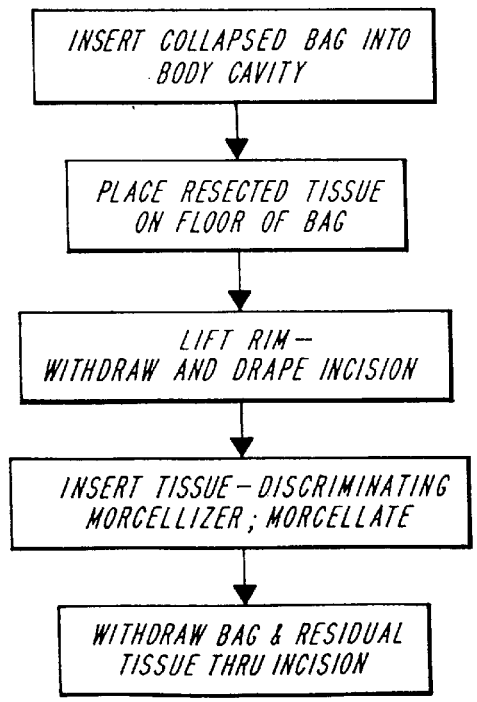
FIG. 8 illustrates the method of the invention.

Skipping ahead to FIG. 8, the method of use of the present invention, briefly, is to insert the bag 10 to a surgical site 40 following the performance of an operation. Excised tissue is then moved onto the tray-like bag on the floor of the surgical cavity, and the top rim of the bag is then drawn back up through the incision 50.

Figure 4A:
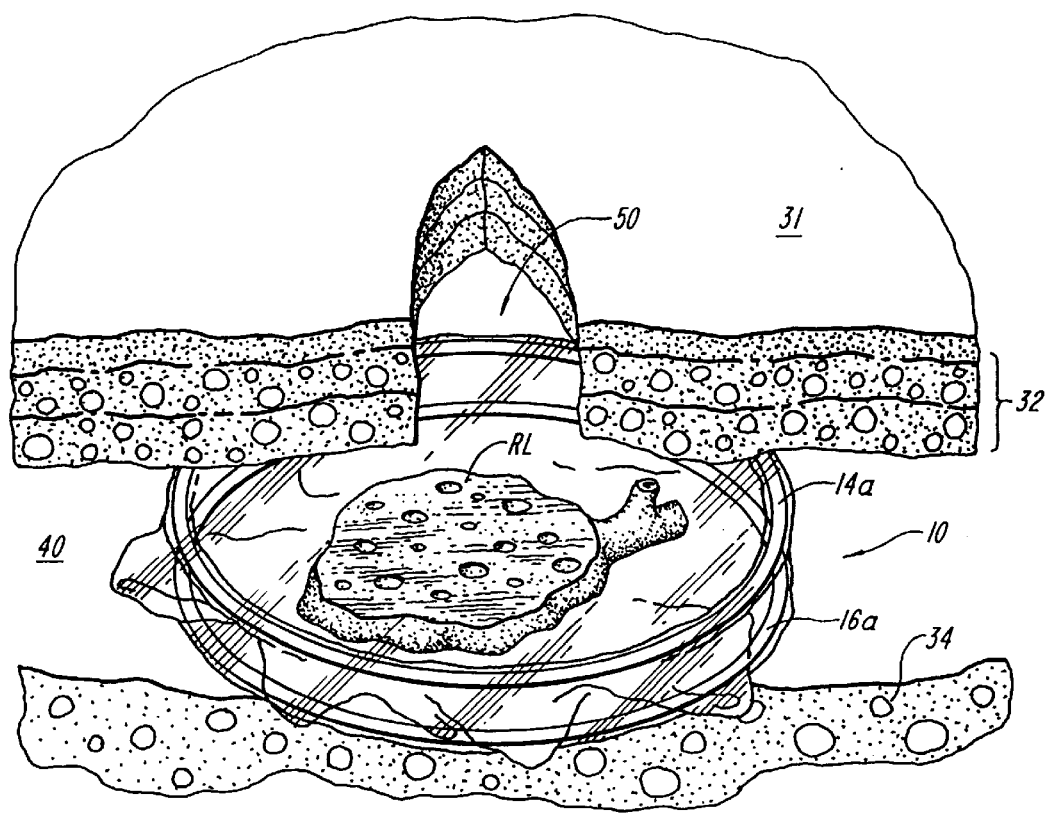
FIG. 4A illustrates the inserted bag after receiving excised tissue.
Figure 5:
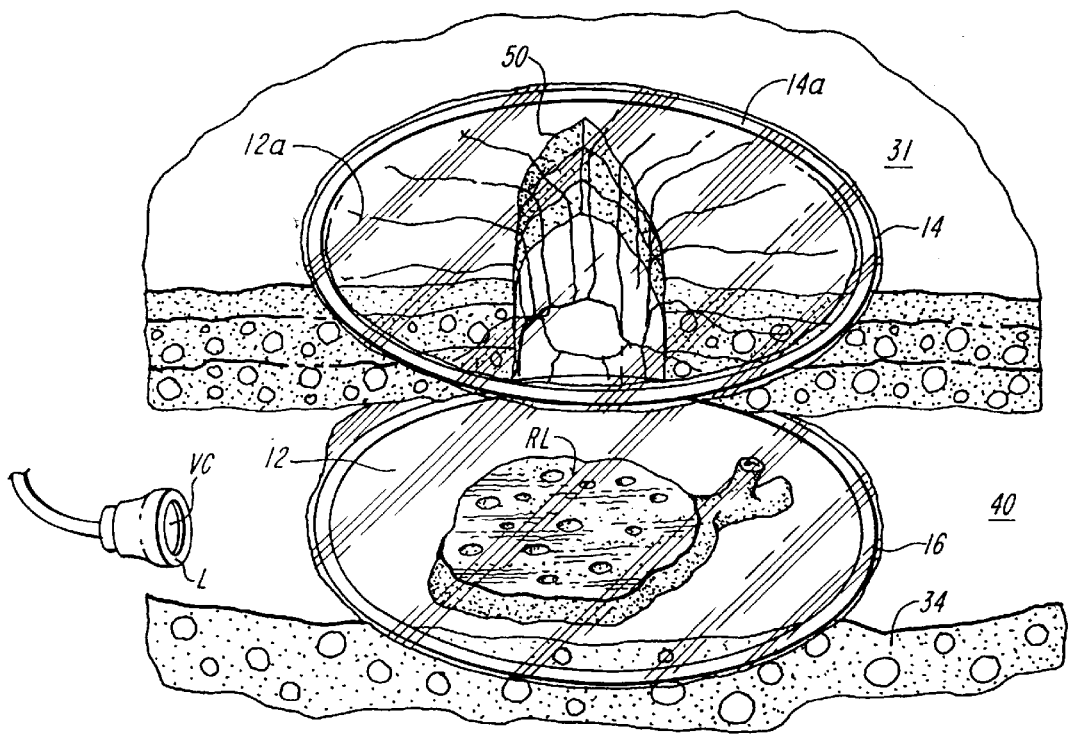
FIG. 5 shows the bag of FIG. 4 partially withdrawn.

FIGS. 4A and 5 illustrate these latter two steps. In FIG. 4A a mass of resected lung tissue RL has been moved onto the flat floor 18 of the bag. After this stage the mouth of the bag is drawn back out through the incision 50. FIG. 5 illustrates the bag in this semi-withdrawn position. As shown, the top rim 14 is withdrawn back out through the incision 50, and it again spreads open so that the bottom rim 16 is suspended or rests on the floor 34 of the cavity 40 while the top rim 14 rests on the skin 31 of the patient, outside the surgical cavity. In this configuration, a portion of the peripheral wall 12 extends from the bottom of the cavity 40 up through the incision, and the outside portion is folded over or lies flat against the skin so that the inside surface 12a of the bag extends around and drapes a band around the surgical incision, and also extends through the incision as the lining of a tunnel leading down into the cavity. As before, the illustrated bag is transparent, and thus poses no obstacle to viewing the tissue held inside. Thus, the endoscopic video camera VC and its illumination source L may effectively illuminate and view the tissue from within the chest cavity. Thus in accordance with a principal aspect of the present invention, the bag is utilized to form a protective chamber around the tissue which has been placed in it.

Figure 6:
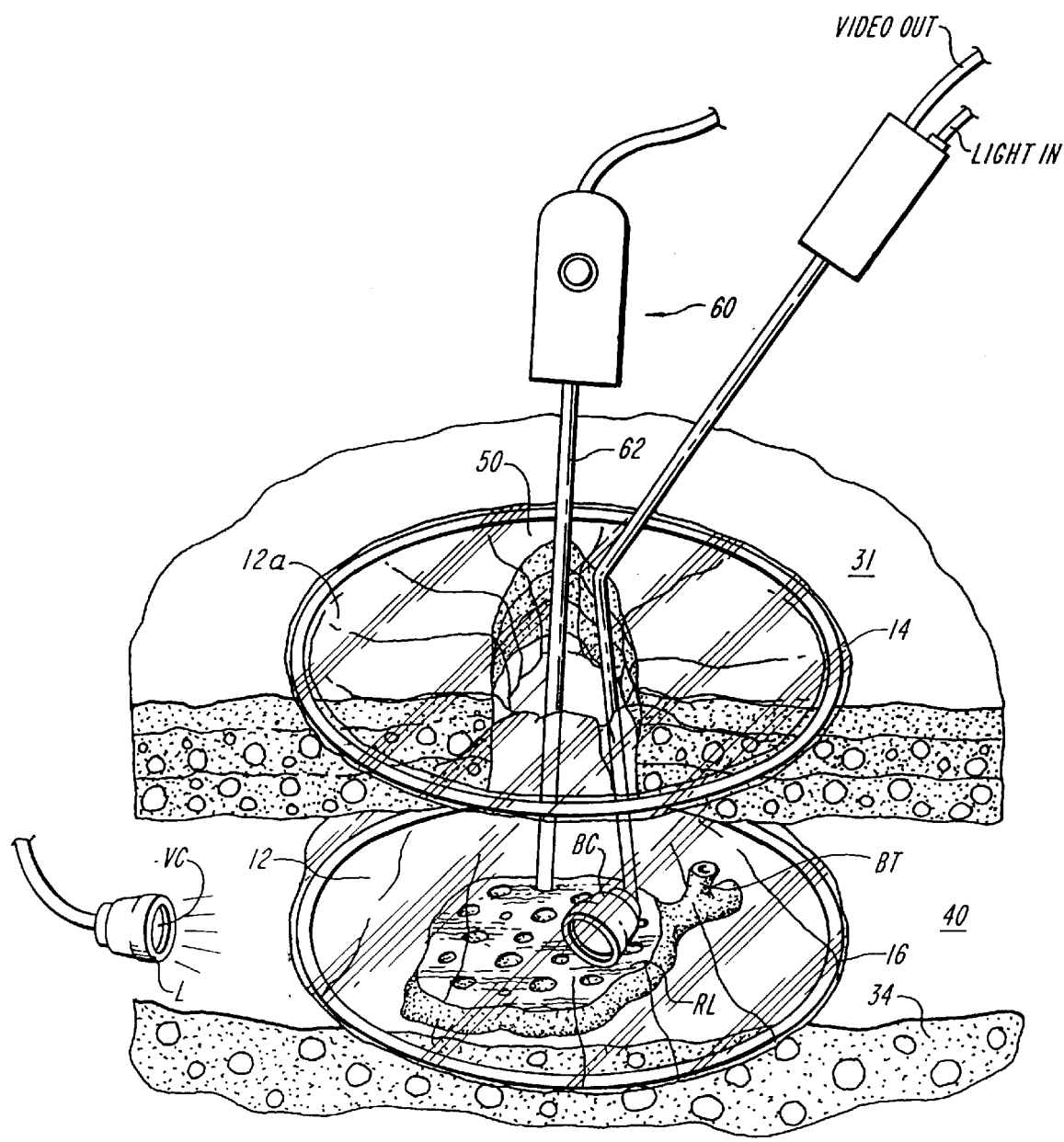
FIG. 6 illustrates tissue morcellation in the bag of FIG. 5.

Illustratively, when employed for thoracoscopic surgery, the bag may receive a portion or an entire lobe, or more of lung tissue. FIG. 6 illustrates this method of use of the bag. In this illustration, the piece of resected lung RL has been moved onto the floor 18 of the bag, and sits entirely contained within the chamber formed by the floor 18 and the surrounding lower portion of the wall 12. A morcellizer 60 is then introduced so that the neck 62 of the morcellizer extends into the tunnel at the incision 50, and down against the resected tissue RL, and the cutting tip of the morcellizer 60 presses against the tissue RL. In practice, the method of the invention involves illuminating and viewing tissue in the bag 10 while the morcellizer morcellates and removes the tissue, thus reducing the contents of the bag while it resides in the cavity 40, without contaminating the cavity 40.

As noted above, the independent endoscopic video camera and light VC, L may be used to observe this process through the transparent wall 12 of the bag. Alternatively, a video camera may be separately inserted directly into the bag along with the morcellizer shaft and cutter assembly, where it may directly view and guide the morcellation, as shown by bag camera BC drawn in FIG. 6. Such direct "bagoscopy" allows a closer-focus camera to be used, with full and detailed visualization to guide the tissue being morcellized. When a camera is so inserted to the morcellation site, it is important to not then replace the camera directly in the body cavity, or to subsequently allow the camera to directly contact tissue. This constraint may be addressed by using a separate camera when in-bag viewing is desired, or by providing a protective sock over the camera during in-bag deployment, so that the camera may be re-used without cleaning once the sock is removed. In any case, the video camera is of some assistance in guiding morcellation of the bagged tissue. As shown, the resected lung includes adjacent tissue, namely the bronchial tree BT. The resected lung is limp and soft, while the bronchial tree is relatively hard, tough and extremely slippery. Moreover, numerous lymph nodes are attached to the bronchial tree, and it is of some importance for the pathologist to view the histology of this tissue sitting in the bottom of the bag, in order to determine the nature of the tumor and ascertain whether it is capable of, or has already metastasized or spread physically, or entered other tissue.

Figure 7:
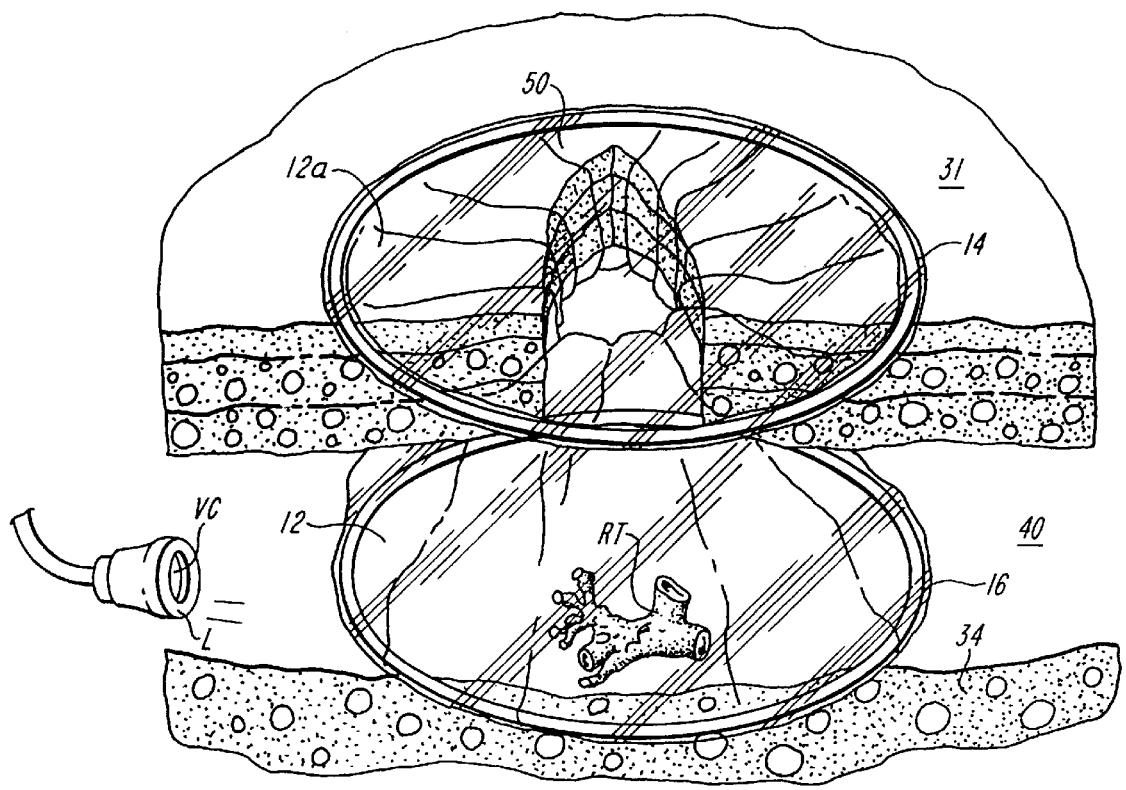
FIG. 7 illustrates tissue residues after morcellation in accordance with the present invention.

Applicant has discovered that when the morcellizer 60 is inserted through the mouth of the tunnel into bag 10, it may be operated in relatively coarse fashion grossly viewing the tissue, and will nonetheless automatically restrict its chopping aspiration preferentially to the parenchyma while leaving intact the bronchial tree BT and the lymph nodes attached to it. Thus, after a period of operation the morcellizer 60 applied to the resected tissue RL shaves and aspirates essentially all of the soft tissue, unless otherwise discriminated against by the operator, and results in a smaller mass of tissue, mainly a small amount of residual tissue RT as shown in FIG. 7. Applicant has found that this residual tissue consists essentially of the bronchial tree and attached lymph nodes with possibly a thin margin of connective tissue from the lung itself. Thus, the relevant harder portions of the excised tissue are automatically left behind in the bag for withdrawal and later examination by the pathologist.

It should be noted that the ability of the morcellizer to discriminate between hard and soft tissue is a specific property of the construction of the morcellizer and is believed to result from the relative size and surface relief of the window which provides an opening to the cutter blade of the morcellizer, and the blade geometry. In the series of experiments described herein, the morcellizer employed was a Model Number PS3500EP motor drive unit made by Smith and Nephew Endoscopy, Inc. of North Andover, Mass., and the cutter blades were relatively large 5.5 millimeter incisor or full radius straight disposable blades, Smith & Nephew blades Model Numbers 4191 or 3444. The morcellizer had a rounded blunt tip with a cutting blade spinning inside a window which subtends approximately thirty degrees of a spherical segment cut out in the rounded tip. With this morcellizer, gentle contact pressure was sufficient to nibble away and entirely aspirate resected lung tissue, while the harder lymph nodes and material of the bronchial tree were essentially unaffected by contact with the morcellizer tip. FIG. 7 illustrates the contents of the bag 10 following morcellation as described above. As shown, the mass of tissue has been greatly reduced and only the small bronchial tree tissue remains with its attached lymph nodes. This is readily removed from the site 40 by withdrawing the bag through the incision.

Continuing with the description of the method of the present invention, following the reduction of tissue mass with the morcellizer, the morcellizer shaft is withdrawn through the opening 50 and the rest of the bag is pulled back up through the incision. This cleanly and finally removes the remaining resected tissue from the body cavity.

One problem addressed by the current invention is the dangerous "seeding" of tumor cells involved in handling any resected tissue. With past devices and techniques, this has been particularly a problem during the step of morcellation when the morcellizer splatters material, ruptures tissue integrity, and may puncture the bag. It has also been a problem when loading the resected material into the bag since contact with exterior surfaces is difficult to avoid. On both of these points the present invention offers distinct advantages. By having a large spring-open mouth rather than the prior art narrow neck, resected tissue may be lifted and dropped cleanly in the center of the floor of the bag. Furthermore, during all subsequent stages of handling, i.e., morcellation and withdrawal of the bag, the mouth of the bag has been already withdrawn back through the incision and the only contaminated surfaces reside outside of the surgical cavity, i.e., either outside the body, or entirely enclosed within the bag. Thus, the only potential routes for contamination are the following:

i.) contact during the initial surgery and resection;

ii.) contact during closing the mouth of the bag and withdrawal back through the incision; and iii.) puncture and defects of the bag itself.

The invention contemplates several further aspects of bag design to address the second two potential sources listed above. These include the fabrication of the bag of a relatively stiff material which does not crinkle into a contour that would be engaged by the morcellizer cutter opening; and the fabrication of a multi-layer bag preferably with a dye marker or other telltale to indicate when wall integrity has been breached. However, even more basic protection against cutting of the bag wall is provided by the basic construction described above, wherein the floor is a flat sheet and the rim 16 around the base assures that the wall 12 extends to and remains substantially near the perimeter of the device. With this construction, when excised tissue is first placed on the floor of the bag (FIG. 2) it is likely to come into contact only with a few small bends or pleats of the wall at the periphery. Moreover, these are deep interior portions of the bag which would not contact the body once the mouth 14 has been raised back up. The construction further guards against tissue contamination by the nature of the spring-like rim bands 14*a*, 16*a* and the nature of their folded insertion or removal. The O-rings may be simply folded once along a diameter to reduce their size by half. It is also possible, as shown in FIG. 3, for each of these bands to be twisted once or folded over on itself to reduce the bag to a flat mass having dimensions approximately ½ or ¼ of its normal diameter. By twisting or folding the rings to collapse them, e.g., into a figure eight, a D, or a folded figure eight, the mouth of the bag is essentially covered by multiple layers of the external wall and the rims themselves provide slight stiff protruding edges which guard against the inner walls rubbing in contact with the tissue adjacent to the incision 50. As already noted above, once the mouth of the bag is withdrawn back out through incision 50 (FIG. 5) the upper portion of the bag provides a continuous transparent drape around the access incision as well as a curtain barrier against direct tissue contact.

Figure 9A:
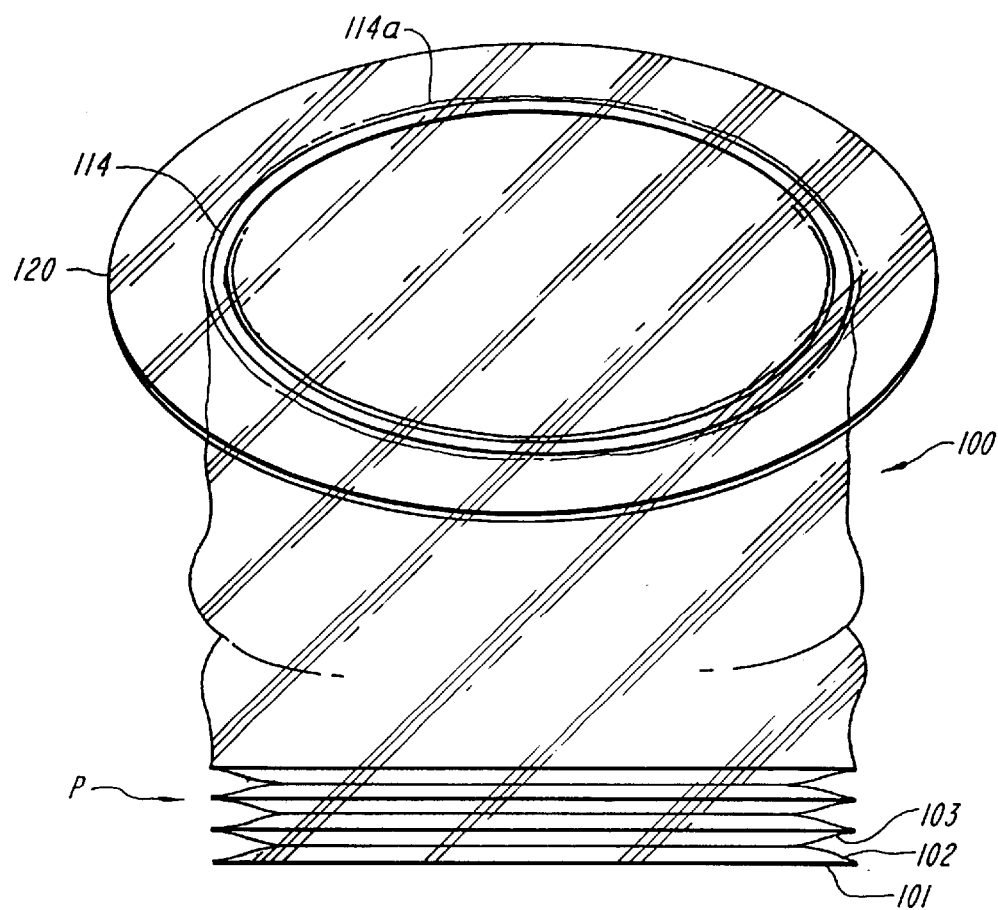
FIGS. 9A–9C illustrate a second physical embodiment of the retrieval bag and details of its construction.
Figure 9B:
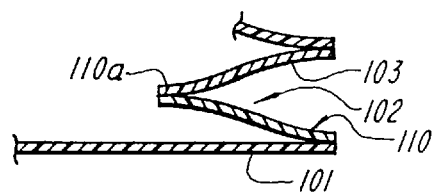
Figure 9C:
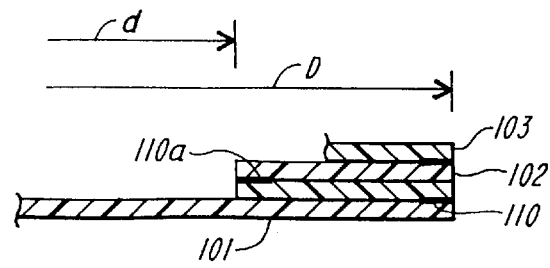

A second embodiment 100 of the invention is shown in FIG. 9A. In this embodiment 100, all or a portion of the bag is formed with a lateral wall including a number of pleats P. By way of illustration, the pleats P are shown as extending along approximately the bottom third of the bag. However in other embodiments the entire bag may be pleated from top to bottom, or fewer pleats, for example two pleats, may be formed at the bottom. FIGS. 9B and 9C show detailed views of pleat construction in the bag of FIG. 9A. In this bag a continuous disc of sheet polymer is provided to form the bottom 101 of the bag. This may for example be a disc of polyvinyl chloride, silicone rubber or similar material approximately one quarter to one half millimeter thick, and having a disc diameter of approximately five inches. An annular ring 102 of similar sheet material having an outer diameter of five inches and an inner diameter one half to one inch less is welded along a circumferential seam 110 to the floor 101 at its outermost periphery. A similar annular ring of sheet material 103 is welded at its inner edge along a seam 110a to the inner edge of annulus 102. Further annular rings are welded along their outer and inner edges of their lower and upper sides respectively. In this manner an accordion-like bellows or series of pleats is built up as shown in FIG. 9B and 9C.

It should be observed that each of the weld seams 110, 110a . . . has a width of several millimeters over which the doubly-thick wall material is joined solid. The inner weld seams (e.g. 110a) are the only points of the peripheral wall that might contact the laterally-directed morcellizer cutter blades, and these seams present a large-diameter concavely-curved edge of thick material which extends radially as a solid horizontal ring for several millimeters. This construction limits the side-to-side motion of the morcellizer and effectively resists perforation, especially when used with a morcellizer blade which is unable to cut harder materials as described above. Thus the weld seams of this pleated construction not only provide an optimal shape, but function as bumpers, ribs or stent rings that protect the bag wall from the morcellizer blade. Advantageously, each of the annular rings, 102, 103 . . . lies in a narrow band around the circumference of the bag, and when the top is not positively held up, the annular sheet washers or rings collapse and lie flat as shown in FIG. 9C providing a relatively rigid circumferential frame about the floor 101. This provides a shallow rim or boundary wall about the floor, which thus sits like a tray or shallow dish on the floor of cavity 40. Furthermore, since the upper, straight portion of the wall (if one is provided) extends for a relatively small part of the height, when the upper part of the bag collapses it forms relatively small folds and wrinkles that also remain in a narrow band around the perimeter of the bag, and are not prone to contact resected tissue in the center of the floor 101, or to spread contaminants. As further shown in FIG. 9A, a collar 120 in the form of a flat sheet is attached to the periphery of the bag 100 at its top edge 114, to drape the surgical incision 50. With this construction, the collapsed bag essentially sits like a stack of punched out annular paper rings, and may be folded over itself to form a flat bundle for insertion through the incision 50. For completeness, an O-ring 114a, similar to spring 14a of FIG. 1, is shown in the top rim. Such a spring allows the bag to be easily gripped and manipulated for removal from the cavity 40. However, the bag may be provided with no extrinsic rim spring, since the flat collar 120 provides a sufficient degree of circumferential stability and rigidity in the mouth region, while still allowing the bag to be folded about an axis for insertion or removal of the bag.

In all of the above embodiments, the bag is characterized by having an essentially cylindrical shape, and the bag relaxes naturally along its longitudinal axis to lie flat in the chest cavity when otherwise unsupported. In collapsed form the side walls essentially lie in a narrow band about the perimeter so that the flat bag sits like a tray or cup to receive excised tissue. Furthermore, the bag lacks the narrow neck of prior art retrieval bags, and instead has a relatively broad and substantially uniform diameter. In other embodiments, the mouth may taper inward or outward to a pleated region to provide a better draping surface externally of the incision, or to provide a collapsed state in which excised tissue is easily loaded into the bag without contacting the upper portions of the bag wall.

Thus it will be seen that the retrieval bag of the present invention advantageously provides a large open receiving surface, and extends to form a large tissue viewing and morcellation chamber, without compromising the requirement of strictly containing the tissue and preventing seeding of diseased cells. The invention has been described as including a spring-open mouth, or an opening defined by a flat sheet or collar. However, other stent or stiffening structures may be employed, and these may include joints or articulations or any suitable type known in the art. The bag may further include a purse string, a spring hinge, or other mechanism for initiating or maintaining closure of the mouth. The bag may be made of diverse materials, generally including surgical grade plastics such has polyvinyl chloride, polyethylene terphthalate, polyurethane and silicone rubber materials, and may be specially formulated in one or more ways to resist damage from the morcellizer, to decrease reflections in the luminous environment of the operating cavity, or to otherwise enhance ruggedness, transparency, or other useful aspects of the bag described above. Bag constructions involving multiple layers, or layers activated to respond with a tell-tale indicator when punctured may advantageously be employed.

The invention being thus described, variations and modifications of the embodiments described herein will occur to those skilled in the art, and all such variations and modifications and equivalents thereof are included within the scope of the invention, as set forth in the claims appended hereto.

What is claimed is:

1. A tissue retrieval bag for retrieving tissue from an endoscopic surgical site, such bag comprising a floor a wall continuous with said floor around its periphery and rising from the floor to a top edge so as to form a substantially cylindrical bag forming a chamber when vertically raised, and a collapsible member in said wall, said member holding the wall in an open ring configuration and spreading the floor so that it forms a tray adapted for receiving excised tissue wherein said member is collapsible for insertion or removal of said cylindrical bag through an incision to the surgical site.

2. A tissue retrieval bag according to claim 1, wherein at least an upper portion of said wall is limp such that when the upper portion is withdrawn from the surgical site through the incision, it drapes the surgical site in a band about said incision while forming a tunnel lined by said wall for protecting the incision from contact with tissue during accessing the interior of said bag and removal of the excised tissue.

3. A tissue retrieval bag according to claim 2, wherein the collapsible member includes a portion of said wall comprising a plurality of annular sheets bonded together to form a pleated circumferential wall such that the bag collapses neatly into a flat stack without wrinkling.

4. A tissue retrieval bag according to claim 3, wherein the bag extends to a top edge, and further comprising a collar at said top edge that forms draping surface for said surgical incision.

5. A tissue retrieval bag according claim 1, wherein said bag and said wall are formed of a material resistant to morcellation when contacted by a morcellizer.

6. A tissue retrieval bag according to claim 1, wherein said collapsible member includes an O-ring defining a substantially constant diameter orifice, and said member collapses by folding to close the bag to a reduced size for insertion through an incision.

7. A tissue retrieval bag according to claim 1, further comprising means for closing the bag.

8. A tissue retrieval bag for endoscopic use, such bag comprising a floor, and a side wall continuous with the floor said continuous side wall being attached to the floor and including a perimeter stiffener that stiffens and maintains the side wall in an outer perimeter band such that the bag collapses flat in a surgical cavity to form a tray-like receiving surface adapted for receiving excised tissue said bag further being foldable to allow passage through an incision to said cavity and having a top portion of the side wall which opens to drape the incision after withdrawal of the top portion therethrough.

9. The tissue retrieval bag of claim 8, wherein the perimeter stiffener includes at least one ply of material joined to the side wall about its perimeter.

10. The tissue retrieval bag of claim 9, where said at least one ply of material includes pleats.

11. A tissue retrieval bag for endoscopic use comprising a floor and a side wall joined to the floor, said floor and said side wall each being formed of polymeric sheet material, said side wall forming a generally cylindrical tube with wide mouth at an end opposite said floor, and a collapsible spring effective to spread said floor so that the floor lies flat and the side wall collapses around the periphery of the floor to form an open tray, whereby excised tissue may be dropped on the floor to enter the bag without pushing or manipulation of the bag during endoscopic surgery.

12. A tissue retrieval bag according to claim 11, further comprising protective ribs extending around an interior portion of said side wall for protecting against puncture.

13. A method of retrieving tissue from a surgical site in a body cavity, such method comprising the steps of forming an incision to access the body cavity inserting a compacted tissue retrieval bag into the body cavity and opening the bag such that its floor lies flat and the bag is spread open within the cavity placing excised tissue in the open bag; and withdrawing a top portion of the bag back through the incision such that the top portion drapes about the incision and provides a tunnel through said incision into the cavity that protects the incision from contact with tissue.

14. The method of claim 13, further comprising the step of inserting a morcellizer through said tunnel to the interior of the bag.

15. The method of claim 14, further comprising the step of endoscopically viewing while morcellating tissue contained in said bag interior.

16. The method of claim 15, wherein the step of morcellating includes morcellating with a cutter that selectively morcellates soft tissue.

17. The method of claim 16, wherein said tissue is lung tissue and the morcellizer has a cutting blade that leaves at least one of bronchial tissue and lymph node tissue unmorcellated.

18. The method of claim 17, further comprising the steps of removing the morcellizer back through said tunnel, and withdrawing the bag containing unmorcellated tissue out of the body cavity through said incision.

19. The method of claim 15, wherein the step of endoscopically viewing includes introducing an endoscope through said tunnel to the interior of the bag, and viewing through said endoscope.

20. The method of claim 15, wherein the bag is formed of transparent material and the stop of endoscopically viewing includes viewing through the wall of the bag with an endoscope located in said body cavity while morcellating tissue.

* * * * *

UNITED STATES PATENT AND TRADEMARK OFFICE
CERTIFICATE OF CORRECTION

PATENT NO. : 5,769,794
DATED      : June 23, 1998
INVENTOR(S): A. Conlan et al.

It is certified that error appears in the above-identified patent and that said Letters Patent is hereby corrected as shown below:

On the title page;

Please add to the References cited section (56) the following foreign patent document:

DE 42 42 153 A1    6/1994     Germany

Signed and Sealed this

Twenty-fifth Day of August, 1998

Attest:

BRUCE LEHMAN

Attesting Officer

Commissioner of Patents and Trademarks